United States Patent [19]
McDowell

[11] Patent Number: 6,056,777
[45] Date of Patent: May 2, 2000

[54] METHOD AND DEVICE FOR REGENERATING CARTILAGE IN ARTICULATING

[76] Inventor: Charles L. McDowell, 7650 Fox Crossing La., Richmond, Va. 23294-4309

[21] Appl. No.: 09/104,657

[22] Filed: Jun. 25, 1998

Related U.S. Application Data

[60] Provisional application No. 60/076,253, Feb. 27, 1998.

[51] Int. Cl.⁷ .............................. A61F 2/30; A61F 2/38; A61F 2/40
[52] U.S. Cl. .............................. 623/18; 623/902; 623/19; 623/20
[58] Field of Search .......................... 623/18, 16, 19–20, 623/22–23, 902

[56] References Cited

U.S. PATENT DOCUMENTS

| | | |
|---|---|---|
| 4,285,071 | 8/1981 | Nelson et al. . |
| 4,385,404 | 5/1983 | Sully et al. . |
| 4,417,571 | 11/1983 | Nelson et al. . |
| 4,880,429 | 11/1989 | Stone . |
| 5,007,934 | 4/1991 | Stone . |
| 5,108,441 | 4/1992 | McDowell . |
| 5,116,374 | 5/1992 | Stone . |
| 5,158,574 | 10/1992 | Stone . |
| 5,306,311 | 4/1994 | Stone et al. . |
| 5,368,051 | 11/1994 | Dunn et al. . |
| 5,612,028 | 3/1997 | Sackier et al. . |
| 5,645,593 | 7/1997 | Woods et al. . |

FOREIGN PATENT DOCUMENTS 2933-174  4/1980  Germany .

*Primary Examiner*—Mickey Yu
*Assistant Examiner*—Choon P. Koh
*Attorney, Agent, or Firm*—Susan L. Firestone; Paul W. O'Malley

[57] ABSTRACT

A prosthetic shield and its method of use are used to repair damaged joints and regenerate cartilage. The shield protects the articulating surfaces of the joint from compression and frictional stresses to protect the bone from further damage and allow cartilage to grow. The shield can be left in place or removed after the joint heals.

21 Claims, 4 Drawing Sheets

METHOD AND DEVICE FOR REGENERATING CARTILAGE IN ARTICULATING

1. Cross Reference to Related Application

This application claims the benefit of U.S. provisional application Ser. No. 60/076,253, filed Feb. 27, 1998.

FIELD OF THE INVENTION

The present invention relates to a method and device for regenerating cartilage in articulating joints.

DESCRIPTION OF THE PRIOR ART

The skeleton has specialized joints for different types of movement. Joints have two or more bones that articulate with respect to each other. Joints extend and flex as hinges like the fingers. They rotate like the ball within the socket of the hip.

The bones of a healthy joint are not actually seated against one another during movement. A layer of articular cartilage usually separates joint bones. Articular cartilage decreases the stress on the bones during motion and subsequently the wear and tear of the bone over a lifetime of movement.

Both friction and compression are often present during movement. Walking upright, for example, places both compressive and frictional stress on the hip. The weight of the upper body pushes down on the joint while the leg rotates within the hip.

Frictional stress is due to the relative movement of two objects. In this case, bone moving against bone generates a great deal more frictional stress than is the case when articular cartilage is present. Without articular cartilage, the surfaces of the bones are exposed, friction increases and movement becomes more difficult. If the bone is covered with cartilage, the bones smoothly glide on the cartilage and movement is easier. By reducing friction, articular cartilage eases movement.

Bones of the joint are not only stressed by movement and friction. Articular cartilage cushions bones against compression. Compressive stress compresses bones by the pressure of bone against bone, such as the weight of the body pushing against the bone or the force of one bone pushing against another.

Disease and injury damage articular cartilage. Osteoarthritis, chondromalacia and rheumatoid arthritis erode the cartilage from the joint. Injuries such as bone fractures can tear or bruise the cartilage, which can also lead to cartilage loss.

The loss of articular cartilage increases friction and compression during movement. The remaining articular cartilage rapidly degenerates under these stresses which causes the bones of the joints to touch against one another directly. The movement of exposed bone against bone further degenerates the articulating surfaces of the bones in the joint to decrease mobility and increase pain.

Repairing damaged joints may require joint replacement. Surgical repair of the damaged joints, such as hip replacement with a prosthesis, is a major operation. Surgical replacement, especially of large joints, is painful and traumatic, often resulting in substantial blood loss and requiring a lengthy recovery period. Furthermore, surgical replacement often requires the surgeon to strip away the cartilage attached to any remaining bone to properly insert and fit the prosthesis. This leaves the joint with little if any remaining articular cartilage.

The cells of native articular cartilage do not regrow in situ. However, if the damaged cartilage is removed and the bone is wounded, such as by grinding, the joint reheals. The wounded bone serves as a source of stem cells, such as endothelial cells and other pleuripotential cells, and chondroblasts. The stem cells grow out of the wounded bone and produce a layer of cartilage. This newly grown cartilage serves to protect the joint bones from friction and compression, much like native articular cartilage does.

Alternatively, stem cells can be transplanted to the joint. These stem cells can be harvested either in vitro from cell culture or in vivo from other parts of the body.

Whether from wounded bone or transplantation, fragile stem cells subjected to compressive or frictional stresses do not grow and form a layer of cartilage. The stresses placed on the growing cells at the surface are great, comparable to growing cells under a moving rock that scrapes and grinds.

The prior art does not adequately address the problems of protecting the stem cells from compressive and frictional stress. A hip replacement, for example, replaces the damaged femoral head and reams the acetabulum to fit the new femoral prosthesis. The prosthetic femoral head directly contacts and rubs against the raw acetabulum with each movement.

Prior art protective caps inadequately protect delicate stem cells. These caps provide a smoother surface which reduces friction during movement. This reduction of friction is decreased, however, whenever the bones move against any irregularity in the surface of the bone, such as peaks or valleys. Furthermore, the caps have little effect on the reduction of compression. The force of bone against bone still bears directly on the stem cells.

Therefore, one object of the invention is to shield the surface of the bone to decrease the compression and frictional stresses and aid in the regeneration of cartilage.

Another object of the invention is to repair the joint without requiring joint replacement.

Another object of the invention is to provide access to stem cells from the bone.

Another object of the invention is to provide a protected surface for grafted materials to attach and grow, such as fibroblasts, chondroblasts, fetal tissue, periosteum and artificial cartilaginous-like materials.

SUMMARY OF THE INVENTION

The invention relates to the repair of articulating joints using prosthetic shields. In one embodiment of the invention, the shield is a curved trough shaped to extend along at least a portion of the articulating surface of a first bone of the joint. The trough has inner and outer surfaces and opposite ends. A spacer head receiving groove is located in the outer surface of the trough and preferably extends from one end to the other. A spacer can be located on a second bone opposite the trough, with the spacer head fitting within the groove.

Alternatively, the shield can be a cap. The cap has a concave inner surface and a convex outer surface and is shaped to fit at least a portion of the articulating surface of a first bone of the joint. When the cap is placed over the bone, a gap forms between at least a part of the concave surface of the cap and the bone's surface. The cap may have a fastener with a fastener shaft and means for separating the fastener and the inner concave surface.

Additional effects, features and advantages will be apparent in the written description that follows.

DETAILED DESCRIPTION OF THE INVENTION

Several aspects of the invention are described in the figures. To aid in understanding the invention, several figures show the invention in situ with the joints separated.

Figure 1:
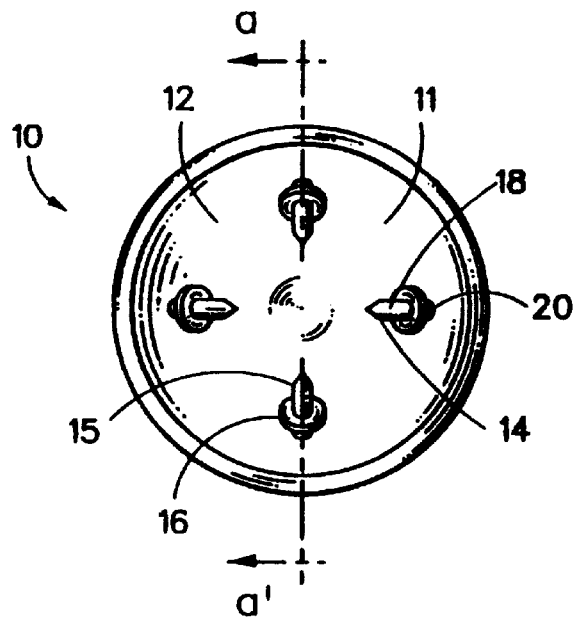
FIG. 1 is a plan view of a shield of the invention.
Figure 2:
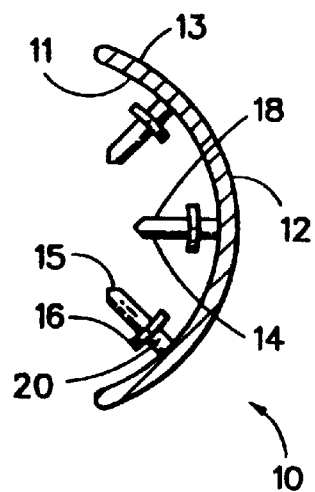
FIG. 2 is a cross-sectional view along lines a-a' of a shield of the invention.
Figure 3:
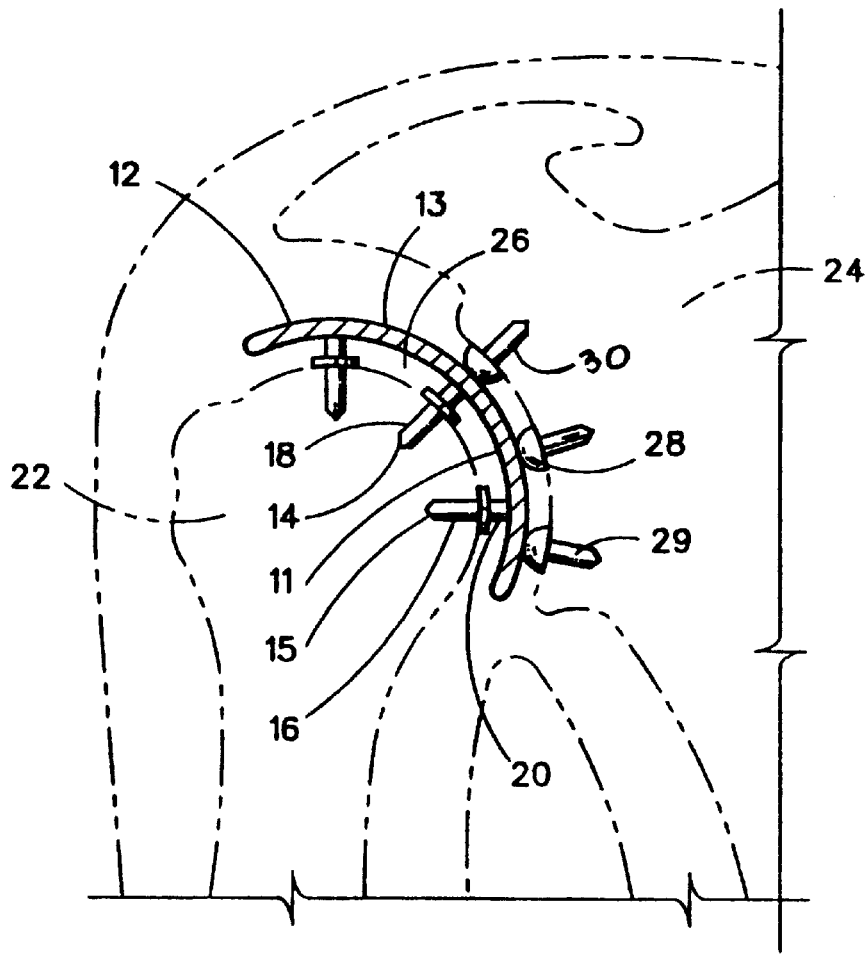
FIG. 3 is a cross-sectional view of a shoulder using a shield of the invention.

FIGS. 1, 2 and 3 show shield 10 of the invention that fits over a bone of an articulating joint, such as the ball of a ball and socket joint. Shield 10 is shaped and sized to conform to the end of the bone. Cap 12 has a concave interior surface 11 and convex exterior surface 13. Cap 12 is typically secured to the bone using fasteners 14, 15, such as screws, pins, pegs, and the like. Fastener 14 has shaft 18 which can have flexible flanges, serrations, threads, pins or slots to facilitate implantation by any method, such as press-fitting, screwing or driving into the bone with a mallet. Head 16 is preferably part of the fastener and is typically flat. Alternatively, head 16 may be a disc, ring, band or grommet attached to and/or encircling the fastener shaft between the bone and the cap. When part of the fastener, head 16 stops the fastener at a desired distance within the bone. Usually a stem 20 is located between head 16 and cap 12 and is preferably part of the fastener. Heads or stems separate at least a portion of the concave surface of the cap from the bone. Heads, stems and the cap are typically smooth, although they may be textured or chemically treated to enhance the regrowth of articular cartilage, such as by providing a site for cellular attachment.

Referring to the shoulder shown in FIG. 3, the head of the humerus 22 has shield 10 implanted opposite the glenoid of scapula 24. Shield 10 covers humeral head 22 and has screw-type fasteners. Stem 20 separates humeral head 22 from cap 12 to form gap 26.

Preferably, a plurality of spacers is disposed between the articulating surfaces as described in U.S. Pat. No. 5,108,441 issued to Charles L. McDowell, which is incorporated herein in its entirety by reference. Spacers 28, 29, 30 are implanted in the glenoid of scapula 24 opposite humeral head 22. Preferably spacers 28, 29, 30 are arranged equidistant in glenoid 24 to form a "pocket" to receive the shielded humeral head 22. More preferably spacers 28, 29, 30 are arranged in glenoid 24 to create a tripod "pocket" to seat the round shield 10 implanted in humeral head 22.

Shield 10 and spacers 28,29,30 keep the articulating surfaces of the joint separated. This facilitates the regeneration of articular cartilage between the articulating surfaces in the shoulder joint by protecting the surface of the humeral head from rubbing against the spacers or opposite bone.

Although the preferred embodiment of the shield is shown fully assembled with cap, fasteners and stems in place, the shield can be part of a kit where the individual parts are assembled before or during surgery. Stems and heads can be individual components, part of the fastener or attached to the cap.

Figure 4:
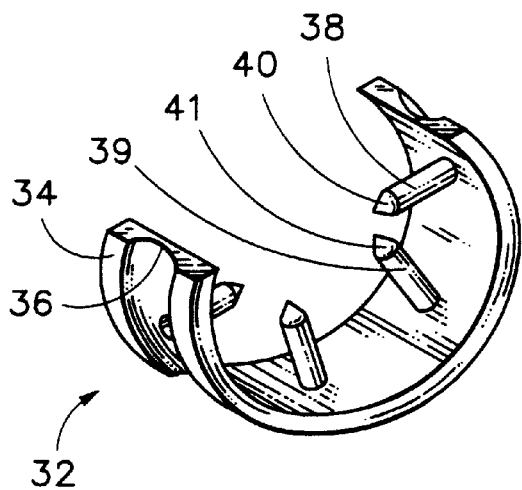
FIG. 4 is a perspective view of a shield of the invention rotated from lateral to the posterior position.

Another form of the invention shields hinge joints, such as the knee, elbow or finger as shown in FIG. 4. For hinge joints, shield 32 has trough 34 with spacer head receiving groove 36. Trough 34 extends over at least a portion of the articulating surface of the bone of the joint, such as the condyle of the femur or the head of a metacarpal or phalanx. The trough is designed to fit the shape of the bone of the chosen joint, for example, a femoral condyle. A spacer head receiving groove 36 is in the outer surface of the trough and preferably extends from one end of the trough to the other.

Trough 34 implants to the bone with fasteners 38, 39. Fasteners 38, 39 have fastener shafts 40,41 which can have flexible flanges, pins, threads, serrations or slots and are implanted by any method, such as press-fitting, screwing or driving into the bone with a mallet. If desired, a head, such as a fastener head, or a disc, ring, band or grommet attached to and/or encircling the fastener shaft between the bone and the trough can be used. The head can separate the inner surface of the trough from at least a portion of the articulating surface of the bone. Although the entire shield is shown fully assembled with a trough and fasteners in FIG. 4, the shield can be part of a kit where the fasteners, heads and the trough are separate pieces assembled before or during surgery.

Figure 5:
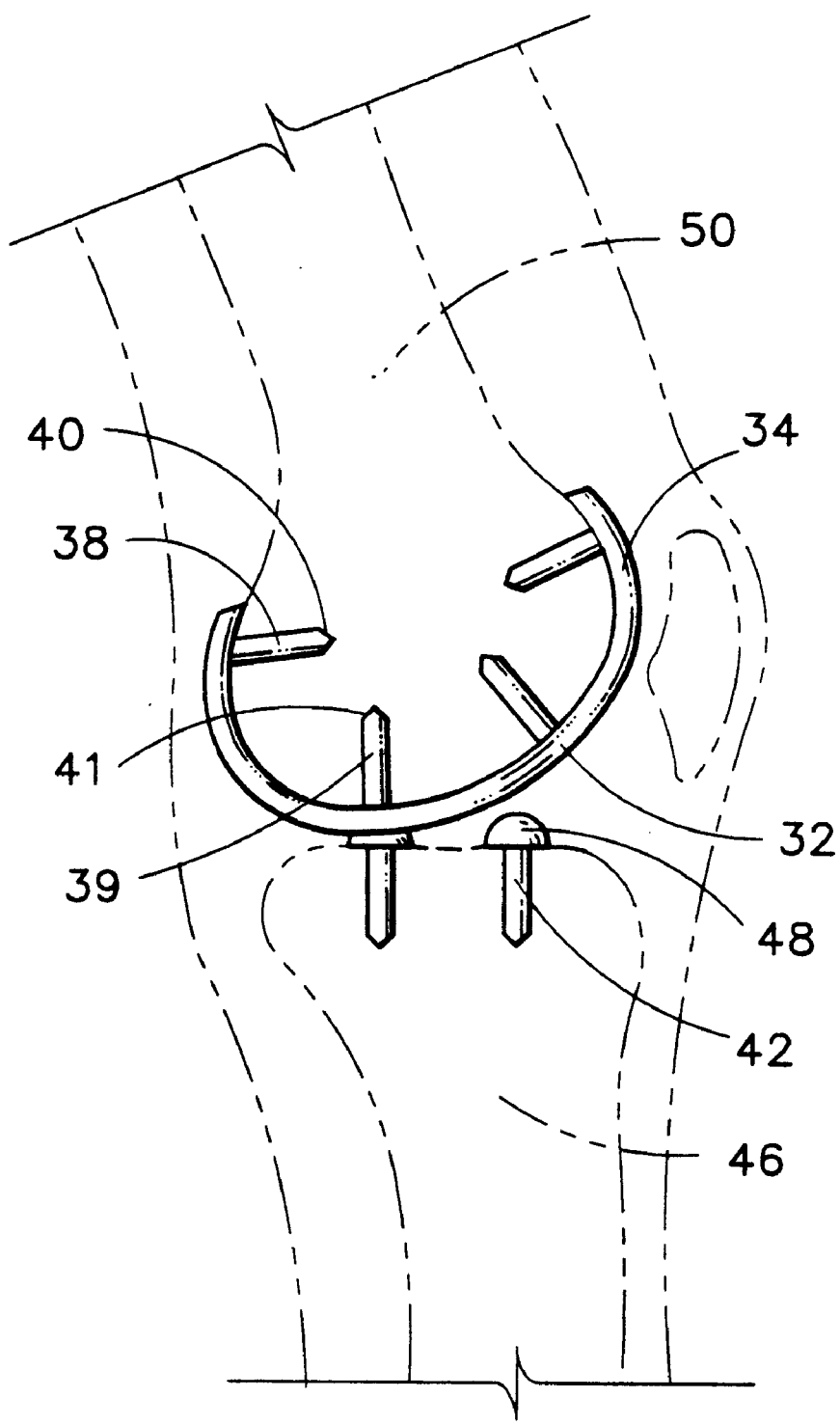
FIG. 5 is a lateral view of a knee using a shield of the invention.
Figure 6:
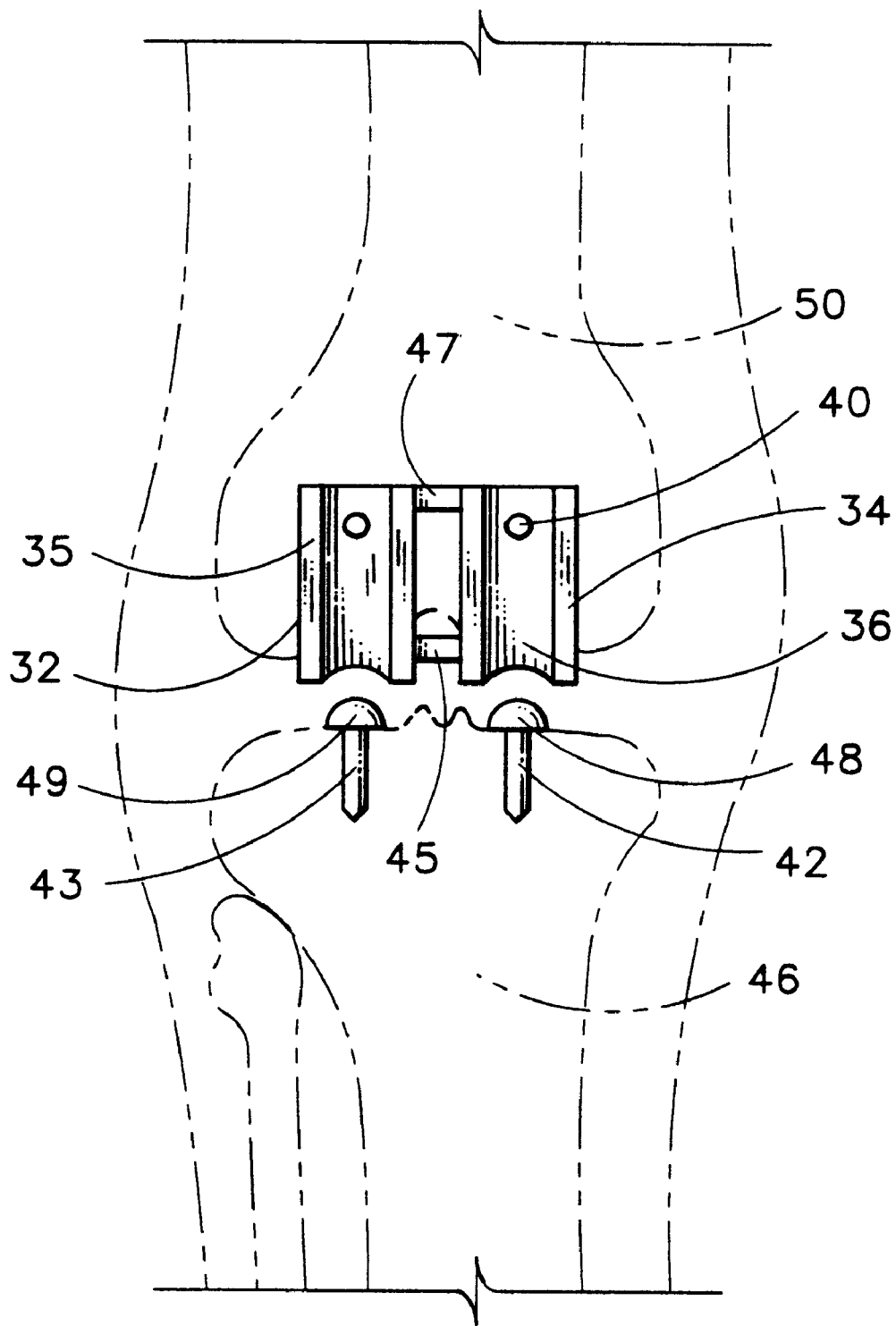
FIG. 6 is a posterior view of a knee with a shield of the invention.

FIGS. 5 and 6 show the shield of the invention implanted in a large hinge joint. In a knee, spacers 42, 43 are implanted in the condyles of the tibia 46, preferably near the tubercles of intercondylar eminence. Spacers 42, 43 have heads 48, 49 that extend from the bone. Spacer heads 48, 49 are preferably domed. Troughs 34, 35 are implanted on the condyles of the femur 50 opposite spacers 42, 43. Trough 34 is oriented so that groove 36 receives spacer head 48. Similarly, trough 35 is oriented so that groove 37 receives spacer head 49 and is parallel to trough 34. Troughs 34, 35 extend around the articulating surface of the condyles of the femur 50 and cup the condyles. When the hinge joint moves, the spacer head tracks within the groove. Preferably, troughs 34, 35 are interconnected, for example, an anterior bridge and posterior bridge 47 positioned between the troughs to preserve their proper alignment within the joint. If desired, additional interconnections such as a medial bridge 45 may also be used to preserve the alignment of the troughs within the joint.

Figure 8:
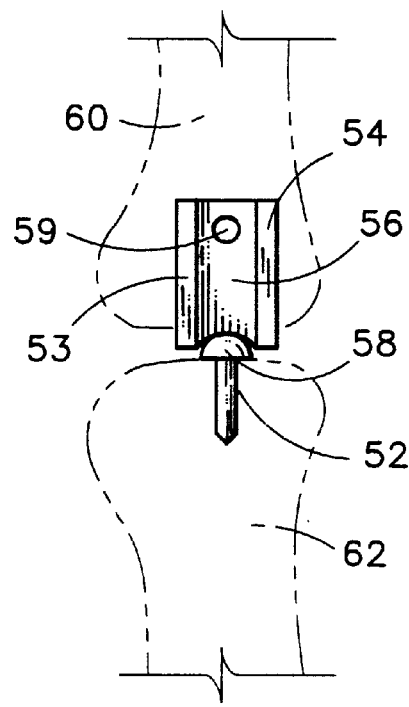
FIG. 8 is a plan view of a finger with a shield of the invention.
Figure 7:
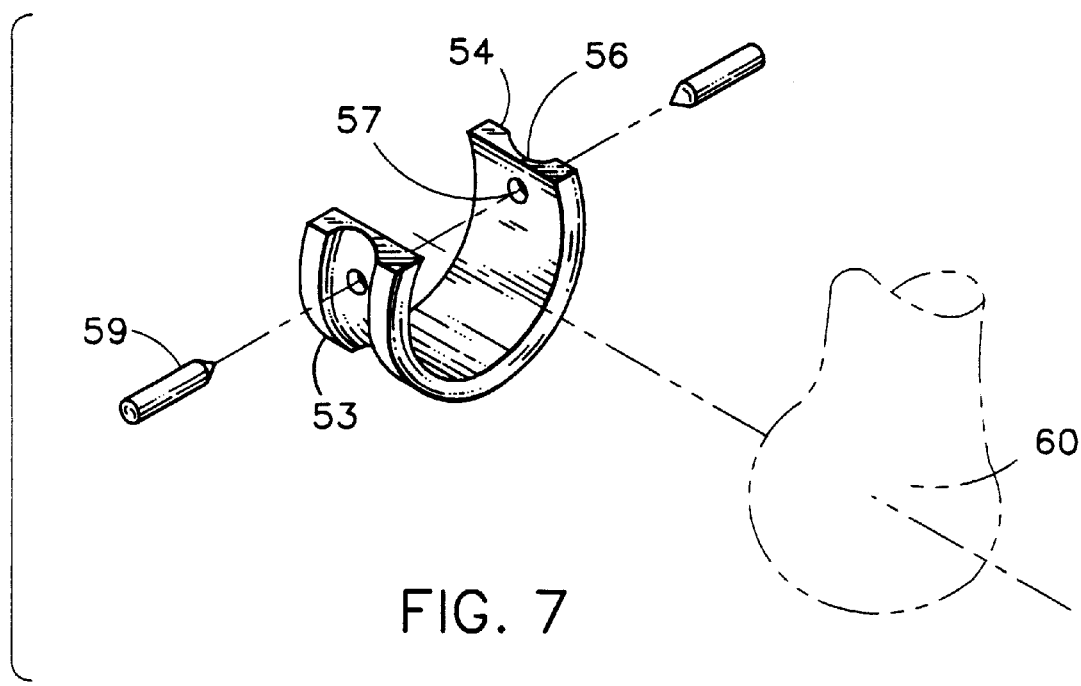
FIG. 7 is an exploded perspective view of a bone with a shield of the invention.

Small hinge joints can use the shield and a spacer similarly to that described for the knee. FIGS. 7 and 8 show a finger with spacer 52 implanted in the base of phalanx 62. Shield 53 implants on the head of the metacarpal 60 opposite spacer 52. Trough 54 is oriented so that groove 56 receives spacer head 58. Trough 54 extends around the articulating surface of the metacarpal head 60. When the hinge joint moves, the spacer head tracks within the groove. If desired, shield 53 may have fastener opening 57, such as a bore, to receive fastener 59.

In one method of the invention, after first separating the bones of the articulating joint, a gap forms between a shield covering at least a portion of the articulating surface of a first bone of the joint. Typically, the shield is implanted with fastener shafts in the bone. The bone is preferably abraded to remove damaged bone and tissue. The bone may also be prepared by making fastener receiving openings for the fastener shafts, such as by drilling, and inserting the fastener shafts into the fastener receiving openings. Preferably, the shield is located opposite spacers implanted in the opposing second joint bone.

When the shield is a cap with fasteners and stems as one integral piece, the shield is implanted into the bone by any known method, such as by using self driving fasteners with flexible flanges that can be press-fitted into place. If the cap contains stems, the stems are seated onto the heads of the fasteners and are affixed in place by any medically approved method, such as cementing. Alternatively, the fasteners may have the stems already attached and the cap is seated onto the stems or directly onto the heads. The cap is preferably affixed to the stems or heads by any medically approved method. The socket bone of the socket joint preferably has spacers implanted, more preferably the spacers are implanted at equidistant intervals to form a "pocket" to receive the shielded head of the ball of the joint. Most preferably the spacers are positioned to form a tripod "pocket" to seat the shielded head.

When the shield is attached to a bone within a hinge joint, the shield has a trough. The trough has a groove to receive the head of a spacer implanted in the opposite bone of the joint. The trough extends along at least a portion of the articulating surface of the bone and is designed to fit the bone into which it is implanted. The trough is preferably held in place by fasteners which are preferably connected to the trough. If the joint is large, such as the knee, two parallel troughs are used as the shield and are preferably interconnected together at the ends. Each groove of each trough receives at least one spacer head of a spacer implanted in the opposite bone.

The shield of the invention is made from any medically approved material which has some rigidity and does not collapse under the stresses present in the joint over time. Suitable materials include metals, such as titanium and stainless steel, and organic polymers, for example, high density polyethylene, ultrahigh density polypropylene, polymeric polylactic acid, and the like. If desired to enhance cell growth and cartilage production, the shield and spacers can be chemically treated.

During surgery, cartilage producing stem cells can be accessed by removing all damaged cartilage or scar tissue from the bone surface. Alternatively, the stem cells can be transplanted to the site, for example, grafting on the surface of the bone. Cells could also be attached to the shield itself before implantation. The cells can be transplanted from other parts of the body or harvested from in vitro cell cultures. New tissue growth can be enhanced by using temporary tissue substitutes or synthetic cartilage as a substrate, for example, biodegradable polymers like SIS, a polymer derived from small intestinal submucosa (available from Purdue University, Warsaw, Ind. and DePuy, Inc., Warsaw, Ind.).

After new cartilage has grown between the joints, the shields and spacers may be removed. If biodegradable materials are used, the material degenerates over time. The removal of the shield and spacers leaves a completely natural joint in which the damaged cartilage between bones has been replaced by new healthy cartilage.

The shields and the methods of their usage of the invention have a number of advantages. The combination of shields and spacers separates and cushions the joints. Like articulating cartilage, the shield and spacer protect the bone from damage caused by compression and friction. The groove of the shield, for example, smoothly allows the spacer head to glide in the groove during movement to reduce friction.

Another advantage of the invention is the production of cartilage. Driving the shaft of the shield into the bone accesses healthy cartilage-producing cells, such as endothelial cells, fibroblasts or condrocytes. Because the invention protects growing cartilage-producing cells by reducing compressive and frictional stresses, the cells grow out of the interior of the bone; and onto the protected surface of the joint. These healthy stem cells can grow into the gap between the shield and bone and produce cartilage.

The shields of the invention also provide a platform to which cartilage-producing materials attach. Whether in vivo or in vitro, stem cells, for example, fibroblasts, chondroblasts, fetal tissue, periosteum and endothelial cells can attach and grow onto the shield. Therefore, artificial cartilaginous-like materials or stem cells can be attached to the shield before implantation and delivered to the joint.

While the invention is shown in only one of its forms, it is not thus limited but is susceptible to various changes and modifications without departing from the spirit and scope of the invention.

What is claimed is:

1. A method of repairing a joint having an articulating surface, the method comprising the steps of:

separating a first bone and a second bone in the joint;

covering at least a portion of the articulating surface of the first bone with a shield with inner and outer surfaces;

forming a gap between at least part of the covered articulating surface of the first bone and the inner surface of the shield;

securing the shield to the first bone and maintaining the gap formed between at least part of the covered articulating surface of the first bone and the inner surface of the shield after securing the shield.

2. A method of claim 1 further comprising the steps of:

implanting a spacer into the second bone; and positioning the spacer to separate the surface of the second bone from the shield.

3. A method of claim 1, wherein the shield is a cap with an inner concave surface and an outer convex surface.

4. A method of repairing a joint having an articulating surface, the method comprising the steps of:

separating a first bone and a second bone in the joint;

covering at least a portion of the articulating surface of the first bone with a shield with inner and outer surfaces;

forming a gap between at least part of the covered articulating surface of the first bone and the inner surface of the shield;

securing the shield to the first bone; and wherein the shield is a curved trough with a spacer head receiving groove located in the outer surface and aligned in the direction of movement.

5. A method of claim 3 further comprising the steps of:

implanting a plurality of spacers into the second bone; and positioning the spacers in a spaced apart relation to separate the surface of the second bone from the cap.

6. A method of claim 3, wherein the gap is formed by placing the cap onto a stem or a head and the cap is secured by implanting a fastener.

7. A method for repairing a joint having an articulating surface, the method comprising the steps of:

separating a first bone and a second bone of the joint;

placing an inner surface of a curved trough over at least part of the articulating surface of the first bone;

aligning in the direction of movement a spacer head receiving groove located in an outer surface of the trough; and securing the trough to the first bone.

8. A method of claim 7, wherein the trough is secured by implanting a fastener.

9. A method of claim 7 further comprising the steps of:

implanting a spacer into the second joint bone opposite the trough; and positioning a head portion of the spacer within the spacer head receiving groove.

10. A method of claim 7 further comprising the step of:

interconnecting an additional curved trough with the trough.

11. A method of claim 7 further comprising the steps of:

placing an inner surface of an additional curved trough over at least part of the articulating surface of the first bone;

aligning in the direction of movement a spacer head receiving groove located in an outer surface of the additional trough; and securing the additional trough to the first bone.

12. A method of claim 11 further comprising the step of:

interconnecting the additional trough with the trough.

13. A prosthetic shield for an articulating joint comprising:

a curved trough shaped to fit at least a portion of an articulating surface of a first bone of the joint, the trough having an inner surface, an outer surface, a first end and an opposite second end; and a spacer head receiving groove located in the outer surface of the trough.

14. A prosthetic shield of claim 13 further comprising:

a fastener receiving opening extending from the spacer head receiving groove through the inner surface.

15. A prosthetic shield of claim 13, wherein the spacer head receiving groove extends from the first end to the second end.

16. A prosthetic shield of claim 13 further comprising:

a fastener extending from the inner surface of the trough.

17. A prosthetic shield of claim 13 further comprising:

an additional curved trough connected to the curved trough, the additional curved trough shaped to fit at least a portion of the articulating surface of the first bone of the joint, the additional curved trough having an inner surface, an outer surface, a first end and an opposite second end;

and a spacer head receiving groove located in the outer surface of the additional curved trough.

18. A prosthetic shield of claim 17, wherein the spacer head receiving groove extends from the first end to the second end.

19. A prosthetic shield for an articulating joint comprising:

a cap with a concave inner surface, a convex outer surface, and shaped to fit at least a portion ofthe articulating surface of a bone ofthe joint;

a fastener having a fastener shaft; and means for separating the fastener from the inner concave surface of the cap.

20. A prosthetic shield of claim 19, wherein the means for separating the fastener from the inner concave surface of the cap further comprise:

a head.

21. A prosthetic shield of claim 19, wherein the means for separating the fastener from the inner concave surface of the cap further comprise:

a stem.

* * * * *